United States Patent [19]

Rawls et al.

[11] Patent Number: 4,515,910

[45] Date of Patent: May 7, 1985

[54] INTERPOLYMERIC RESIN FOR TREATMENT OF TEETH

[76] Inventors: Henry R. Rawls, 3245 DeSoto St., New Orleans, La. 70119; Allan E. Querens, 5652 Marcia Ave., New Orleans, La. 70124; Barbara F. Zimmerman, 632 Phosphor Ave., Metairie, La. 70005

[21] Appl. No.: 461,026

[22] Filed: Jan. 26, 1983

[51] Int. Cl.³ .................. A61K 7/18; C08L 27/12
[52] U.S. Cl. ........................ 523/115; 106/35; 424/151; 523/116; 524/544; 260/998.11
[58] Field of Search ............ 260/998.11; 523/115, 523/116; 524/544; 106/35; 424/151

[56] References Cited

U.S. PATENT DOCUMENTS

| | | | |
|---|---|---|---|
| 3,341,505 | 9/1967 | Gander | 526/287 |
| 3,427,274 | 2/1969 | Cornell | 106/35 |
| 3,625,916 | 12/1971 | Newman | 524/434 |
| 3,925,895 | 12/1975 | Kliment et al. | 433/224 |
| 3,969,499 | 7/1976 | Lee et al. | 433/228 |
| 3,991,008 | 11/1976 | Temin et al. | 528/950 |
| 4,146,608 | 3/1979 | Ritchey | 424/147 |
| 4,155,890 | 5/1979 | Hofacker-Freifrau | 523/115 |
| 4,203,220 | 5/1980 | Cranfield | 433/228 |

Primary Examiner—Ronald W. Griffin
Attorney, Agent, or Firm—Scully, Scott, Murphy and Presser

[57] ABSTRACT

An interpolymeric resin and composition therefrom for treating teeth to prevent dental caries by forming a protective barrier and providing a source of fluoride ions for release adjacent the surface of the tooth. The resin includes an anion-exchange-site bearing monomer carrying fluoride ions, an acrylic comonomer, a cross-linking monomer, and, optionally, a wetting/etching monomer. The resin may have a high degree of cross-linking which then may include filler material to form a composition.

22 Claims, 7 Drawing Figures

INTERPOLYMERIC RESIN FOR TREATMENT OF TEETH

BACKGROUND OF THE INVENTION

The present invention, which resulted from research conducted with the aid of funds granted by the National Institute of Health, relates to the art of dental health and, in particular, to interpolymeric resins useful in the treatment of teeth to prevent and/or inhibit dental decay.

In recent years, efforts in the area of preventive dental therapy have resulted in technology which provides a protective barrier for surfaces of teeth. This type of therapy, which generally includes minimal removal of hard dental tissue cariously involved followed by restoration and/or sealing of the intact or acid-etched surface, has been shown to conserve healthy tooth tissue, reduce treatment time, and provide adequate protection against new caries.

Resins capable of setting (polymerizing and curing) in the oral environment play a primary role in effectuating such treatment. Depending on the nature of the desired results the resins employed in dental treatment should have specific characteristics such as good bonding properties, hardness, and non-degradation in the presence of water, etc. Since these preparations, which are variously characterized as sealant, restorative, and/or adhesive depending on the role they play in the particular treatment, must be capable of infiltrating an acid-etched surface and/or the porosity of carious tissue, the monomers must be highly fluid and have a strong affinity for mineral surfaces. Moreover, the resin must be able to solidify in thin dimensions under oral conditions.

In other dental and biomedical applications polymeric resins are used for constructing various removable and non-removable prosthetic devices and body-part replacements, and for various other purposes. Generally, depending on the desired results, the resins employed for these applications require little or no cross-linking and are not used as adhesives. In many applications in dentistry, prosthetic devices made from these materials interfere with good oral hygiene and, therefore, promote tooth decay and periodontal degradation. Materials for these applications can be formed and cured in situ, or they can be formed externally. In this latter case, the application of heat can be utilized to effect curing and an accelerating agent is not needed. Such materials are variously characterized as prosthetic resins, endodontic filling resins, resin cements, temporary restorative resins, veneering or utility resins, depending upon the role they play in dental or medical treatment. For example, U.S. Pat. No. 3,925,895 to Kliment, et al. describes an acrylic, hydrophilic root canal filling resin and U.S. Pat. No. 4,155,890 to Von Nostiz describes acrylic resins for both heat curing and accelerated curing in a patients mouth to form prosthetic devices.

Dental resins ae usually acrylic materials based on an ester of acrylic or methacrylic acid, typical monomers being methyl methacrylate or a diacrylate of 2,2-bis(p-hydroxyphenyl)-propane, known as BIS-(GMA) resins. The dental resin is normally used as a monomer or as a monomer/polymer mixture, i.e., an incompletely polymerized resin and polymerization is completed in situ when the resin has been placed in position on the dental tissue. Other types of clinically tolerated resins are known and used, e.g., in dentistry or orthopaedic surgery, all of which have polymerizable olefinic double bonds in the molecule. All such resins are available as monomers or monomer/polymer mixtures and include any necessary catalysts etc. so that, after the resin has been put in its final position, completion of polymerization occurs within a few minutes under ambient conditions.

U.S. Pat. No. 4,203,220 to Cranfield describes the use of a bifunctional bridging molecule for bonding dental resins, which are usually acrylic materials based on an ester of acrylic or methacrylic acid, to dental tissue. Specifically, this disclosure shows the use of alkenylamino dihalotriazines which have a group that chemically reacts with the dental tissue and a reactive group that polymerizes with the dental resin.

U.S. Pat. No. 3,341,505 to Gander shows a film-forming composition resulting from polymerization of acrylic or methacrylic esters with certain acrylate or methacrylate amine containing monomers. The esters are of alkyl alcohols containing 1 to 12 carbon atoms, while the amine containing resins are typically reacted with acid ions such as fluoride, chloride, bromide, iodide and sulfate and organic sulfonates which are capable of being attached either directly or indirectly to form the amine salt. The resins can be used as a flexible water soluble film on the skin or as a cement composition for adhering dressings.

Further work in the dental area and, for that matter, in hard tissue technology in general has also provided methods of incorporating medicaments in sealants and/or restorations and/or adhesives such that the medicaments are released from the host composition over a period of time. In U.S. Pat. No. 3,969,499 to Lee Jr., et al. a polyurethane composition containing a fluoride ion is used as a dental tissue sealant which also serves as a topical fluoride treatment for teeth. The composition used in the Lee Jr., et al. U.S. Pat. No. 3,969,499 disclosure is a polymeric reaction product of a hydroxy-terminated butadiene prepolymer and a polyisocyanate reactant, as well as an aromatic polyol in one embodiment, while the source of the fluoride ion is an inorganic fluoride salt which releases fluoride ions by a diffusion/dissolution mechanism.

Similarly, in U.S. Pat. No. 3,625,916 to Newman a "decay-preventing" cement is disclosed which includes primarily an acrylic resin of polymethyl methacrylate and polyethyl methacrylate having an inorganic fluoride. Once again, fluoride is released by a diffusion/dissolution mechanism.

As a result of the teachings in the art in general relative to the mechanism of release of fluoride ions, degradation of the anti-caries adhesive or restorative host resin has been regarded as a necessity to effect topical application of the anti-caries agent.

By the present invention, however, an improved sealant/adhesive/restorative resin has been provided which is readily wettable to the teeth, sets rapidly under oral conditions in a thin layer, and effects topical fluoride release without necessary degradation of the resin.

Furthermore, the mechanism for the amount of, and the time of fluoride ion release is highly controllable.

SUMMARY OF THE INVENTION

According to the present invention there is provided a highly effective fluoride-releasing acrylic interpolymer which delivers fluoride ions by means of a diffusion-controlled anion-exchange mechanism. The interpolymer is a reaction product of an anion-exchange-site bearing monomer which carries fluoride ions and a polymerizable acrylic monomer selected from alkyl acrylates and methacrylates wherein the alkyl group contains no more than about twelve (12) carbon atoms, and a crosslinking monomer. Anion-exchange-site bearing monomers useful herein include aminoalkylacrylates and aminoalkylmethacrylates. When used in dental applications, the amount of fluoride containing monomer included in the interpolymer should be an amount sufficient to provide a caries inhibiting amount of fluoride; up to no more than about 40% of the interpolymer.

In one embodiment of the invention the crosslinking comonomer effects a very high degree of crosslinking in the resulting resin, which can also be combined with a filler material such as silica or silanized silica to form a composition of matter for dental restoration. In order to effect a plastic-like composition to facilitate application to the teeth, a preformed polyalkylacrylate powder may be included with the resin.

While the present invention is presently contemplated as primarily useful as a method of preventing dental caries by impregnation, sealing, or filling of the teeth with the disclosed interpolymers and compositions therefrom, or as a removable oral device for delivering fluoride, it is also believed that this invention is useful in bio-medical applications in general, such as bone cement. Accordingly, all such roles are considered to be within the scope of the present invention.

As a result of the present invention a rapid setting resin has been provided for use in dental applications which is highly wettable to the enamel surface of the teeth, strongly adhesive thereto, high in impact strength, and which delivers anti-carious fluoride ions to the adjacent tooth surfaces to inhibit the progression of caries in the area of such application.

For a better understanding of the present invention, together with other and further objects, reference is made to the following description, taken in conjunction with the accompanying drawings, and its scope will be pointed out in the appended claims.

DETAILED DESCRIPTION OF THE INVENTION

Figure 1:
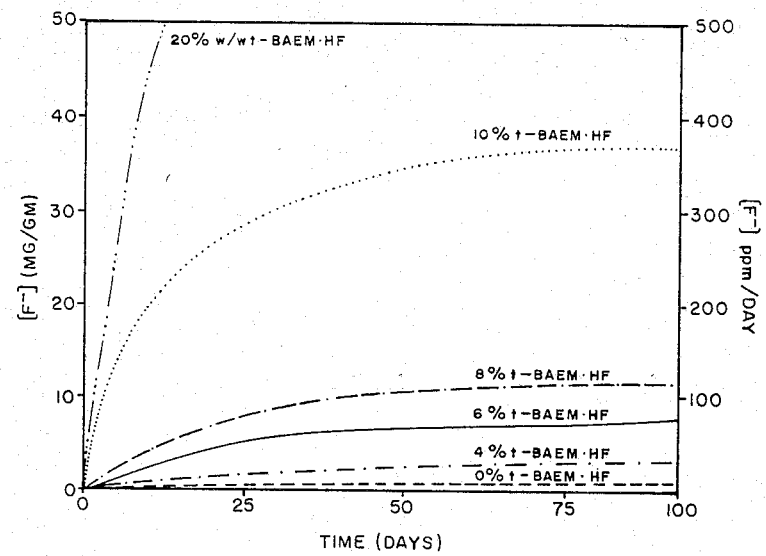
FIGS. 1–3 are graphs showing performance of an unfilled acrylic interpolymer embodiment of the invention.

By the present invention, it has been discovered that an interpolymer resin material highly effective for depositing on dental surfaces (especially those already having carious effects found therein) which also delivers fluoride ions in the oral cavity without necessary degradation of the deposited resin is provided by reacting a monomer having an anion exchange site carrying a fluoride ion with two polymerizable acrylic monomers, one of which is a crosslinker in the resulting resin reaction product.

The use of acrylic materials for dental resins is known. The alkyl radical of the methacrylate or acrylate useful herein contains up to about 12 carbon atoms, and preferably contains from 1 to 5 carbon atoms. Some examples of methacrylates suitable for use in the present invention include methyl methacrylate, ethyl methacrylate, isopropyl methacrylate, butyl methacrylate, capryl methacrylate, palmityl methacrylate, stearyl methacrylate, lauryl methacrylate, Bis-Glycidyl methacrylate (Bis-GMA), 2-hydroxyethyl methacrylate (HEMA), 1,3-butyleneglycoldimethacrylate (BGD). Similarly, acrylate esters having the same alkyl radicals as those of the above methacrylates may be used.

Other acrylic monomers selected for use in the present invention because, among other things, of their respective properties, especially as crosslinking monomers, include but are not limited to ethylene glycol dimethacrylate (EGDMA), trimethylpropane trimethacrylate (TMPTMA), triethyleneglycol dimethacrylate, and polyethyleneglycol dimethyacrylate.

When it is necessary to prepare an interpolymer, and/or a resulting composition, which is required to be particularly resistant to swelling and/or degradation resulting from aqueous imbibition, one of the comonomers should possess high crosslinking properties in the resulting interpolymer. A highly cross-linked structure is advantageous when a strong adhesive is required. Also such resins can be used in filled compositions which are suitable as composite restoratives.

Filler material for incorporation in compositions of the present invention include all those known in the art of effecting high impact strength, resistance to moisture invasion, etc., such as exhibited by inorganic silicates as well as other fillers known in the art. These silicates include amorphous silica, glass, quartz, and alumina. In particular, silica and silane-treated silica have been found to be especially useful with the interpolymers described herein.

Also a preformed resin powder may be included in compositions prepared according to the invention to facilitate handling by formation of a plastic mass. Inclusion of such powder concomitantly reduces the heat produced by exothermic polymerization since the amount of polymerization is lessened, and the degree of shrinkage resulting from polymerization is reduced. Preformed resin powders useful herein include polymethacrylate (PMMA) as well as any copolymers of acrylate and/or methacrylate compatible with the other components and for the intended use. See for example U.S. Pat. No. 3,427,274.

Copolymer acrylic resins for dental application are generally prepared by mixing separate portions of the monomers or comonomers either previously combined without polymerization or in uncombined portions, each of the separate portions having included therein either an initiator or an accelerator. Accordingly, each of the two components, which can be in either a liquid state, or a powder or in a paste form are designated an accelerator portion or an initiator portion. Polymerization of the two monomer reactants occur when both the initiator and the accelerator are present. Thus, the accelerator portion and initiator portion are mixed just before application to the appropriate surface. Inasmuch as no limitation is imposed on the way in which the components are mixed, any other suitable method of combining the ingredients may be used.

In any event, initiators useful in the polymerization reaction include, but are not limited to, benzoyl peroxide, cumene hydroperoxide, etc. Such initiators are well known to those skilled in the art, and it is intended to include all useful initiators.

Similarly, accelerators used in the present invention include, but are not limited to N,N-dimethyl-p-toluidine (DMPT), 1-acetyl-2-thiourea, etc., and the present invention contemplates all useful accelerators presently known in the art. See, for example, U.S. Pat. No. 3,991,008 to Temin, et al.

A third component of the present interpolymer is a polymerizable monomer which contains an anion exchange site capable of carrying a fluoride ion. When reacted in combination with the resin described above, the deposited material forms a diffusion barrier against demineralization, and supplies fluoride in controlled amounts to the oral environment immediately adjacent to the surface of the teeth over an extended period.

Even though any anion-exchange-site-bearing polymerizable monomer capable of carrying a fluoride ion can be used, it has been found that amine-substituted monomers which form weak-base and/or quaternary fluoride salts can be polymerized to form anion-exchanging resins. Typical amine-HF monomers useful herein include alkyl-aminoalkyl acrylates or methacrylates having the following general formula

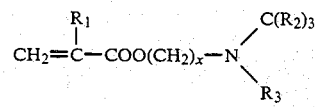

in which
$R_1$ is H or $CH_3$,
X is an integer of 1 to 12,
$R_2$ is H or an alkyl group of $C_1$ to $C_4$, and
$R_3$ is H or an alkyl group of $C_1$ to $C_{12}$.

In one embodiment of the invention the monomer t-butylaminoethyl methacrylate hydrogen fluoride (t-BAEM-HF),

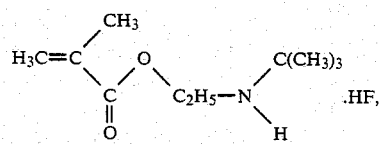

was found to be particularly effective.

Another useful monomer, which is a quaternary fluoride salt, is N,N,N-trimethylaminoethyl-methacrylate fluoride

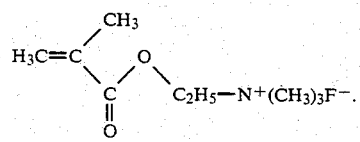

Other ingredients may be included as necessary to achieve particularly good results. For example, it has been discovered that the use of methacrylic acid is especially effective to attain a secure deposition. It is believed that the methacrylic acid acts as a wetting/etching agent in that it alters slightly the surface of the tooth, i.e., "roughens" the surface, so that the liquid reactants will readily adhere thereto, while at the same time the methacrylic acid makes the liquid reaction mixture more compatible with the tooth surface so that the mixture readily spreads or "wets" to such surface with ease. Moreover, inclusion of methacrylic acid, which actually copolymerizes with the other monomers present during the reaction, also accelerates the polymerization reaction, a highly desireable feature for a reaction taking place in the oral environment. Consequently, when the present invention is used in a role requiring a strong bond incorporation of methacrylic acid might eliminate the need for an intermediate acid-etching step.

Further components used in the present invention are polymerization inhibitors in very slight amounts in order to increase storage life and allow time for application to the surfaces requiring treatment before complete polymerization. Examples of such inhibitors are hydroquinones, such as butylated hydroxy toluidine (BHT) and butylated hydroxy anisole (BHA); methyl ether of hydroquinone (MEHQ) has been found to be particularly effective in the present invention.

EXAMPLE 1

One resin without a high degree of cross-linking was prepared according to the formula below.

A two-part liquid/powder commercial resin system having the brand name TRIM (sold by Harry J. Bosworth Co., of Skokie, Ill.) which includes methyl methacrylate and ethyl methacrylate as the principal components in the accelerator-liquid portion and preformed polymethyl methacrylate as the principal component in the initiator-powder portion, was prepared by adding the acrylic fluoride monomer t-BAEM-HF to the accelerator-liquid portion in amounts varying from 0-40% w/w so that in the cured resin product the amount of t-BAEM-HF varied from 0 to 20% w/w. The t-BAEM-HF is believed to have co-polymerized with the acrylic monomers in the TRIM to form an anion-exchange resin with the fluoride ion as the mobile (exchangeable) phase. TRIM powder (i.e., initiator-containing portion) was mixed with the different prepared liquid portions to yield resins containing t-BAEM-HF in amounts of 0%, 4%, 6%, 8%, 10% and 20%.

These resin mixtures were allowed to cure in the form of pellet samples which were tested for loss of hardness, water absorption, and fluoride release. Hardness was measured using a Durometer D-Scale meter. These measurements provided information on the effect of moisture on mechanical properties.

Fluoride ion concentration was measured using an Orion ion-specific electrode. Fluoride ion release rates were monitored with a specific-ion electrode during the moisture uptake experiments. The samples were first soaked in distilled, deionized water to allow escape of all physically entrapped, unbound fluoride. When no further increase in fluoride concentration was noted the solution was changed and a 50% total ionic strength buffer (TISAB) was substituted to encourage the release of fluoride by ionic exchange. Fresh solution was used weekly. When fresh solution failed to stimulate release, the sample was considered depleted and the total amount of fluoride ion released per $cm^2$ of resin surface area was calculated (see FIG. 1). The amount released in buffer is a measure of HF and the fluoride ions present as a salt bound to the resin polymer network.

Figure 2:
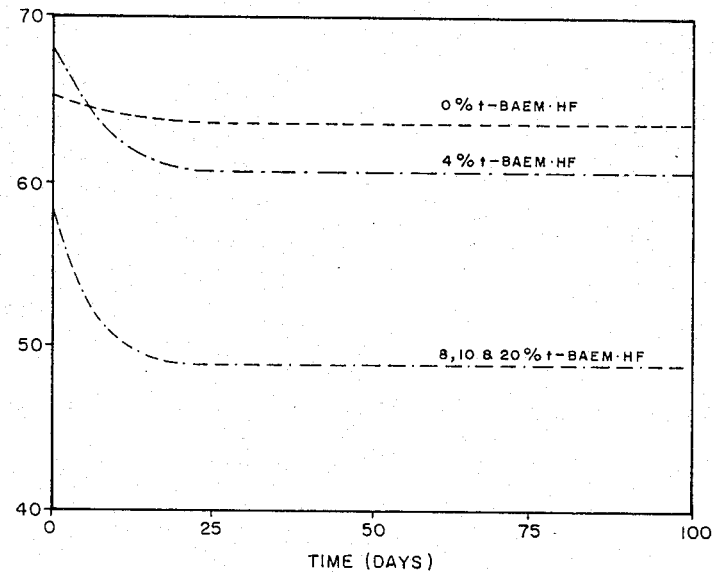
Figure 3:
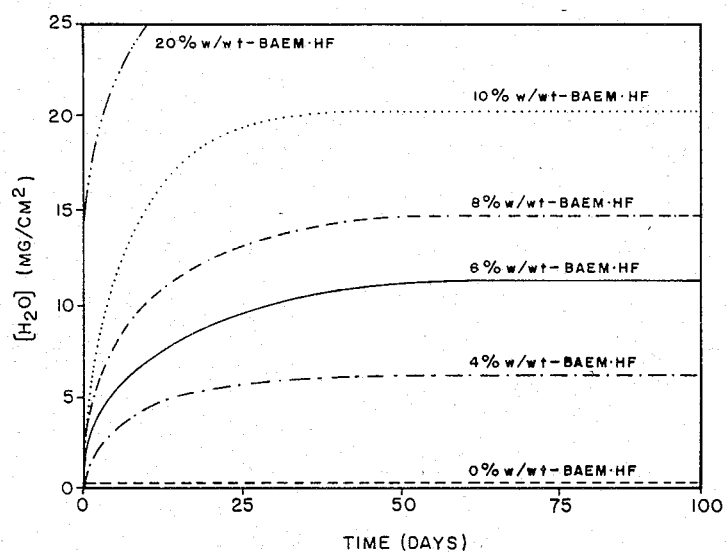

Water absorption, which leads to swelling and fluoride release and is likely to weaken the material, was measured by change in pellet weights as a result of water imbibation at 37° C. TISAB, the TISAB solution being changed weekly. The results of all the above tests are depicted in FIGS. 1-3.

As can be seen from this data fluoride release continued for 4-10 weeks (FIG. 1). At only 4% and 6% of added t-BAEM-HF, an average of 3 and 80 ppm/day of fluoride, respectively, would be released from a 10 gram prosthesis, (assuming a 1 liter/day salivation rate).

While softening and water sorption was rather high at a t-BAEM-HF level above 8% (FIG. 3), both hardness loss and water sorption were moderate for 4% addition of t-BAEM-HF (approximately 3 mg/cm$^2$ water sorption and only 2 units hardness loss). Fluoride release for this level of t-BAEM-HF was in the range of probably therapeutic efficacy.

Consequently, it is believed that a formulation such as that set forth in Example 1 can be employed quite effectively as a fluoride-releasing resin with physical properties ideal for use as a bite-splint or other intraoral removable prosthetic device.

Other resins have been prepared which may be filled or unfilled using powerful crosslinking monomers in accordance with Table I.

TABLE I

| Component | Possible Ingredient | Vol. % Initiator Liquid Portion | Vol. % Accelerator Portion |
|---|---|---|---|
| Fluoride Release Monomer | t-BAEM—HF | Broad 1–40% Preferred 10–30% | Broad 1–40% Preferred 10–30% |
| Comonomer | Glycidyl Methacrylate (GMA) or Ethylene Glycol Dimethacrylate (EGDMA) | Broad 10–90% Preferred 50–75% | Broad 10–90% Preferred 50–75% |
| Crosslinker | Trimethylolpropane-trimethacrylate (TMPTMA) | Broad 0.5–80% Preferred 10–25% | Broad 0.5–80% Preferred 10–25% |
| Accelerator | Dimethyl-p-Toluidine (DMPT) | 0 | 0.01–0.02% |
| Initiator | Benzoyl Peroxide (BP) | 0.02–0.04% | 0 |
| Inhibitor | Methyl Ether of Hydroquinone (MEHQ) | 200–300 ppm | 200–300 ppm |
| Wetting/Etching Agent | Methacrylic Acid (MAA) | 0–33% | 0–33% |

The resins in Table I can be filled with a filler material such as silica. In this way, restorative-type composite resin were prepared. A silanized amorphous silica having an average particle size of 1.55 microns (IMSIL A-10P, Illinois Minerals Co.) was used. It was found that loadings from about 10% to about 90% by weight could be realized while still retaining a clinically-workable consistency.

Another general formula according to the present invention which has a liquid portion and a dry powder portion is seen in Table II. This formula includes generally the type of resins formed by use of TRIM as previously set forth herein.

TABLE II

| Component | Range | |
|---|---|---|
| Liquid Portion | | |
| Fluoride Carrying Monomer | Broad | 1–40% v/v |
| | Preferred | 10–30% v/v |
| Comonomer | Broad | 10–90% v/v |
| | Preferred | 50–75% v/v |
| Comonomer/Crosslinker | Broad | 0.5–80% v/v |
| | Preferred | 10–25% v/v |
| Accelerator | | 0.5–2.0% v/v |
| Inhibitor | | 10–200 ppm |
| Wetting/Etching Agent | | 0–33% v/v |
| Powder Portion | | |
| Resin Powder (May be preformed)* | | 90–99.5% w/w |
| Initiator | | 0.5–2.0% w/w |

*The resin powder can be any polyalkylacrylate compatible with requirements for use in dental applications.

EXAMPLE 2

Samples of a highly crosslinked interpolymeric resin of Table I were prepared for testing as follows:

TABLE III

| Component | Function | *Sample A | Sample B | Sample C | Sample D | Sample E |
|---|---|---|---|---|---|---|
| t-BAEM-HF | Fluoride Release | 17% v/v | 17% v/v | 17% v/v | 17% v/v | 33% v/v |
| Glycidyl Methacrylate (GMA) or | Fluid Monomer | 66% v/v | 49% v/v | 33% v/v | 0 | |
| Ethylene Glycol Dimethacrylate (EGDMA) | Monomer/ Crosslinker | 0 | 0 | 0 | 49% v/v | 33% v/v |
| Trimethylolpropane-trimethacrylate (TMPTMA) | Crosslinker | 17% v/v | 17% v/v | 17% v/v | 17% v/v | 17% v/v |
| Methacrylic Acid (MAA) | Wetting and Etching | 0 | 17% v/v | 33% v/v | 17% v/v | 17% v/v |
| Benzoyl peroxide (BP) | Intiator | 0.01–0.02% v/v | — | — | — | — |
| Dimethyl-p-toluidine (DMPT) | Accelerator | 0.005–0.01 v/v | — | — | — | — |
| Methyl Ether | Inhibitor | 200–300 ppm v/v | — | — | — | — |

TABLE III-continued

| Component | Function | *Sample A | Sample B | Sample C | Sample D | Sample E |
|---|---|---|---|---|---|---|
| of Hydroquinone (MEHQ) | | | | | | |
| Silanized Amorphous Silica | Filler | — | — | **80% w/w | **55% w/w | **55% w/w |

Figure 4:
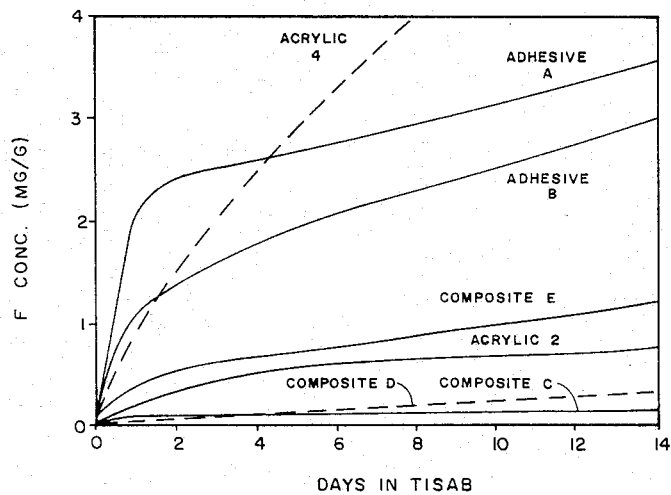
FIG. 4 is a graph depicting the controllability of fluoride ion release by varying different components.

*When referring to FIG. 4, the samples are referred to by their suggested roles, i.e. Low Degree of Crosslinking = Acrylic; High Crosslinking-No Filler = Adhesive; High Cross-linking and Filler = Composite.
**The loading % was calculated based on weight amount of filler/weight amount of total composite.

EXAMPLE 3

Additional samples (1–4) of resin were prepared in accordance with the invention which had a low degree of crosslinking. These samples were prepared once again by the use of TRIM, which is believed to have the following suggested formula:

TABLE IV

| Component | Function | Proportion |
|---|---|---|
| Liquid Portion | | |
| Ethyl Methacrylate (EMA) | Comonomer | 90% v/v |
| Ethylene Dimethacrylate | Comonomer/ Crosslinker | 10% v/v |
| Butylated Hydroxy Toluene | Inhibitor | 50 ppm |
| N,N—Dimethyl-p-Toluidine | Accelerator | 50 ppm |
| Powder Portion | | |
| Polymethyl-methacrylate (PMMA) | Preformed Resin Powder | 99% v/v |
| Benzoyl Peroxide (BP) | Initiator | 1% v/v |

Fluoride-containing monomer t-BAEM-HF was added to the liquid portion of the TRIM, before admixing the liquid and powder portion, in amounts such that the resulting resins contained 0, 4%, 6% and 8% by weight of t-BAEM-HF, respectively, i.e., Sample 1–0% of t-BAEM-HF; Sample 2–4% of t-BAEM-HF; Sample 3–6% of t-BAEM-HF; and Sample 4–8% of t-BAEM-HF.

Certain of the samples from Example 2 and 3 were tested to show the characteristics of fluoride release into 50% total ionic strength buffer (TISAB), the results of which are shown in FIG. 4. As can be seen, the rate of release of fluoride ion is highly controllable by varying numerous factors such as degree of polymerization (which, as is known in the art, can be varied changing the relative amount of initiator relative to accelerator), extent of crosslinking, proportion of hydrophilic monomer present, especially MAA and t-BAEM-HF, and filler loading in the case of composites.

It is believed that in contact with a solution the polymer imbibes water, swells and develops a water phase. Ions diffuse through this water phase to the polymer-chain anion exchange sites where bound positive charges exchange their fluoride counter ions for other anions, whereupon the fluoride ions diffuse out through the crosslinked polymer network.

Further tests were conducted to determine the amount of water sorbed as a result of immersion in water. The results were reported below.

| Water Sorption of Fluoride-Exchanging Resins | | |
|---|---|---|
| Sample | Immersion Time (Days) | Water Absorbed (mg/cm$^2$) |
| C | 0 | 0.0 |
| | ½ | 0.6 |
| | 7 | 0.6 |
| | 14 | 1.7 |
| | 61 | 3.8 |
| D | 0 | 0.0 |
| | 7 | 15.0 |
| | 69 | 20.2 |
| A.D.A. Specification 27 (filled restoratives) | 7 days | <0.7 mg/cm$^2$ |

As indicated above, Sample C absorbed very little moisture, and is well within the A.D.A. Specification. Furthermore, subsequent sorption also remained at a low level.

Other experiments showed that hydrophilic components in the resin samples caused higher water sorption. However, water sorption is necessary to effect fluoride ion release and it appears that water sorption in the present resins does not result in breakdown of the physical properties.

For example, bond strength, and the endurance of the bond which develops between various resins and polished (unetched) human enamel, was determined in water at 37° C. Upper maxiliary incisor teeth were imbedded in dental acrylic with the facial surfaces exposed, and were then ground flat and polished with 600 grit SiC paper. The flattened surfaces where then treated with the resin and held together. A 0.001 inch tin foil spacer was sandwiched between the imbedding-acrylic surfaces while the resin underwent polymerization. This determined the thickness of the adhesive layer. One tooth was cut to form a square about 1 mm on a side, and pressed against the larger flat surface of an opposing imbedded tooth. Also imbedded in the acrylic was a jig to attach the bonded teeth to the crosshead of an Instron Universal testing machine, or to a pulley/weight rig that allowed a constant tension to be applied to the bond while it was stored in water at a controlled temperature. A static stress of 4 kg/cm$^2$ was found to result in bond endurance times that ranged up to 1000 hours. At least two and usually 4 to 6 bonded tooth pairs were prepared for each experimental and commercial formulation to be tested. The results are shown on FIG. 5.

In another experiment bonded pairs were prepared for each formulation and stored in water at 37 C. with no applied tension. After one day and again after two weeks specimens were removed and stressed in tension until the bond ruptured. See FIG. 6. This experiment also included bonding to etched enamel (Epoxylite 35% phosphoric acid etching agent, 60 sec) using the formulation that had exhibited the longest bond endurance under 4 kg/Cm² tension. See FIG. 7.

In all of the bond-strength experiments a commercial fissure sealant, Epoxylite 9075 (Lee Pharmaceuticals), was used as a control resin for comparison. Since this resin is not formulated to polymerize properly in 0.001 inch sections at room temperature, the bonded teeth were heated at 80 C. in air at 100% humidity for one hour. These conditions were also used with the experimental resins, because it was found that in so doing the experimental variation was substantially reduced.

Figure 5:
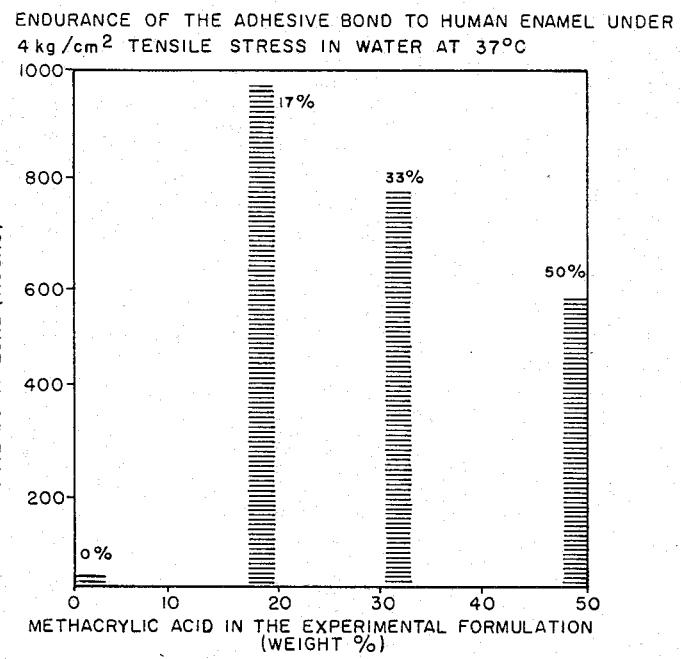
FIGS. 5–7 show the bonding performance of the invention.
Figure 6:
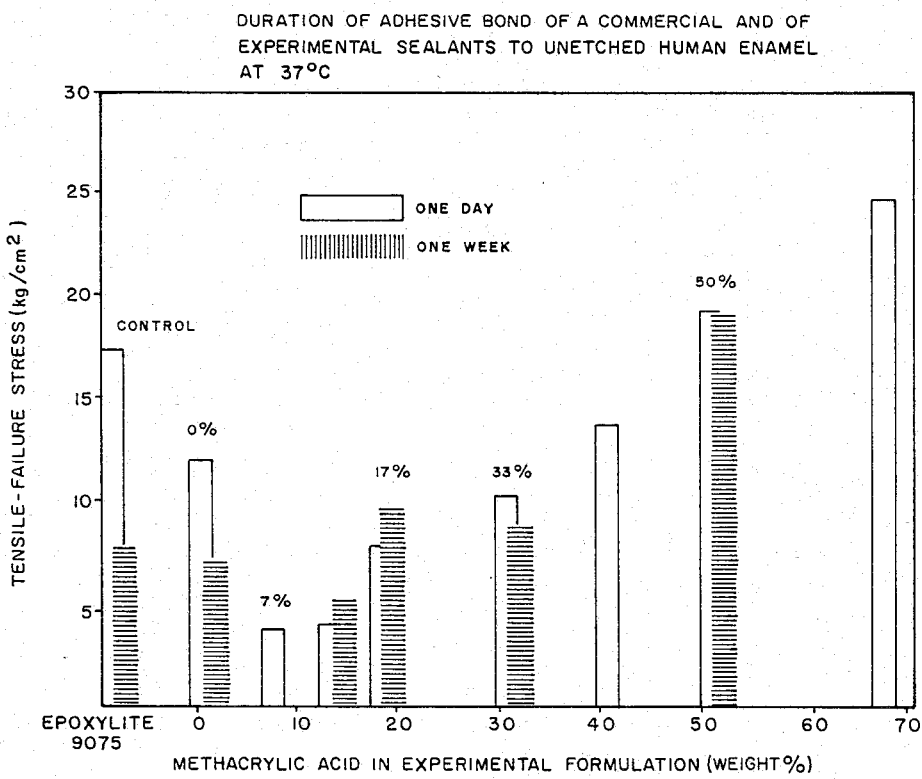
Figure 7:
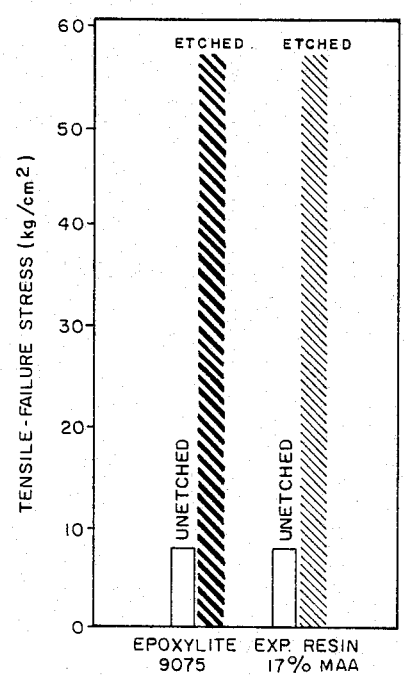

As the proportion of methacrylic acid (MAA) was increased the bond strength to unetched enamel also increased, even if the bond was stored in water for as long as one week (FIG. 6). However, when placed under moderate tensile stress equal to that just required to break the bond formed by the weakest formulation (7% MAA), the endurance of the bond in water has a maximum in the vicinity of 17% MAA, as shown in FIG. 5. After etching, the advantage of MAA in the resin is diminished (FIG. 7). As shown in FIGS. 6 and 7, the 17% MAA formulation is comparable in bond strength and endurance to the commercial pit and fissure sealant Epoxylite 9075.

The ability of the formulations containing methacrylic acid to form relatively strong and enduring bonds without etching is probably related to a "self-etching" capability due to the weak acid nature of MAA. This should prove of use in aiding penetration into natural lesions in vivo. In vivo the presence of pellicle, plaque and debris would hinder penetration. Acid etching is known to help in cleaning these materials away. Thus, it is logical to conclude that MAA or other acidic monomers in a caries-protective formulation would be an aid to adequate penetration.

Caries inhibition of the fluoride resins was also measured using artificial caries systems. Human enamel either sound or already containing an artificial lesion was treated with highly cross-linked GMA based resins using, generally, the Formula shown for Sample B in TABLE III, but varying the level of MAA between 0 and 33% and adjusting the level of GMA accordingly. After the resins had hardened, the excess resin remaining on the tooth surfaces was scraped away. Thus only that resin which had infiltrated the tooth porosity would have remained. The teeth were then stored in a moist electrolyte environment for 10 days and subsequently demineralized.

After a second demineralization of the gel-demineralized teeth, thin sections were cut and various histological features of the lesions, surface zones (SZ) decreased by 75% and lesion bodies increased by 86%, while in resin-treated lesions the SZ remained essentially constant and lesion bodies increased by only 52%. This is shown in Table V.

TABLE V

Lesion progression after resin treatment of demineralized zones

| TREAT-MENT Resin/ % MAA | LESIONS Number Examined | *SURFACE ZONE (SZ) Thickness (Microns) | % change from initial | **LESION BODY Depth (Microns) | % change from initial |
| --- | --- | --- | --- | --- | --- |
| HF/33 | 53 | 15 | −38 | 163 | 57 |
| HF/0 | 59 | 19 | −21 | 158 | 52 |
| Initial | 181 | 24 | 0 | 104 | 0 |
| None | 108 | 6 | −75 | 193 | 86 |

*The surface area of the tooth below which the tissue has become porous.
**Below-surface porous zone resulting from demineralization.

It was also found that the dark zones (DZ) of these lesions were significantly larger than the DZ of untreated, and initial (before treatment) lesions. A significant increase of 38% (average of the two fluoride resin groups) was demonstrated compared to a decrease of 15% in the dark zones of the untreated lesions. This indicates that the second demineralization had no significant effect on DZ except to increase it in the lesions that had been treated with the fluoride resins. This result may indicate a remineralizing effect of the fluoride resin. These results, broken down by each of the treatment groups, are shown in Table VI.

TABLE VI

Dark zone development in resin-treated teeth during lesion progression

| TREAT-MENT Salt/ % MAA | LESIONS Number Examined | Number with Dark Zones | DARK ZONE (DZ) Thickness (Microns) | % change from initial |
| --- | --- | --- | --- | --- |
| HF/33 | 57 | 42 | 42 | 44 |
| HF/0 | 60 | 39 | 38 | 32 |
| Initial | 181 | 133 | 29 | 0 |
| None | 109 | 60 | 25 | −15 |

After initiation of lesions in (treated or not treated) sound enamel, the SZ was essentialy the same for both treated and untreated teeth but slightly larger lesion bodies developed in the treated teeth. After lesions had formed, the dark zones of F-resin treated enamel were significantly larger than in untreated resin-treated enamel.

In a separate experiment the rate of phosphate release from demineralized enamel into a pH 4.5 buffer was found to be decreased by 85% in fluoride resin treated lesions. From these results it would appear that the HF-containing resins present a very effective barrier against continued demineralization.

In summation, the present invention provides a new resin and composition, as well as a method for treating teeth which forms a protective barrier for the surface of the tooth and supplies a source of fluoride ions for controlled release.

Thus, while there have been described what are presently believed to be the preferred embodiments of the invention, those skilled in the art will realize that changes and modifications may be made thereto without departing from the spirit of the invention and it is intended to claim all such changes and modifications as fall within the true scope of the invention.

We claim:
1. An acrylic controlled fluoride releasing interpolymer comprising the reaction product of:

a. an anion-exchange-site bearing monomer carrying a fluoride ion in an amount sufficient to provide a caries-inhibiting amount of fluoride;
b. a copolymerizable acrylic monomer selected from the group consisting of alkyl acrylates and methacrylates wherein the alkyl group contains no more than about 12 carbon atoms; and
c. a monomer which is a crosslinker in the resulting interpolymeric resin.

2. The interpolymer of claim 1 which further comprises a wetting/etching monomer.

3. The interpolymer of claim 2 wherein said wetting/etching monomer is methacrylic acid.

4. The interpolymer of claim 1 wherein said acrylic monomer is included in an amount of from about 10% to about 90% based on the volume of unfilled prepolymerization reaction mixture.

5. The interpolymer of claim 4 wherein said amount is from about 50% to about 75%.

6. The interpolymer of claim 1 wherein said fluoride carrying monomer is included in an amount of from about 1% to about 40% based on the volume of unfilled prepolymerized reaction mixture.

7. The interpolymer of claim 6 wherein said amount is from about 10% to about 30%.

8. The interpolymer of claim 1 wherein said crosslinker is selected from the group consisting of ethylene glycol dimethacrylate, trimethylpropane trimethacrylate, triethylene glycol dimethacrylate, and polyethylene glycol dimethacrylate.

9. The interpolymer of claim 1 wherein said crosslinker is included in said interpolymer in an amount of from about 0.5% to about 80% based on the volume of unfilled prepolymerization reaction mixture.

10. The interpolymer of claim 9 wherein said amount is from about 10% to about 25%.

11. The interpolymer of claim 1 wherein said fluoride carrying monomer is selected from the group consisting of the hydrogen fluoride salt of aminoalkylacrylates and aminoalkylmethacrylates.

12. The interpolymer of claim 11 wherein said aminoalkylacrylates and aminoalkylmethacrylates have the general formula

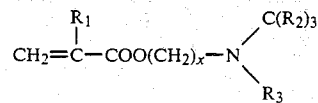

in which
$R^1$ is H or $CH_3$,
X is an integer of 1 to 12,
$R_2$ is H or an alkyl group of $C_1$ to $C_4$, and
$R_3$ is H or an alkyl group of $C_1$ to $C_{12}$.

13. The interpolymer of claim 12 wherein said fluoride carrying monomer is t-butylaminoethyl methacrylate hydrogen fluoride.

14. The interpolymer of claim 12 wherein said fluoride carrying monomer is N,N,N-trimethylamino ethylmethacrylate fluoride.

15. A composition of matter comprising the interpolymer of claim 1 which is highly crosslinked and a filler in an amount of from about 10 to about 90% based on the total weight of said composition.

16. The composition of matter of claim 15 wherein said filler is an inorganic silicate.

17. The composition of matter of claim 16 wherein said filler is one of silica, silanized silica, glass and quartz.

18. The composition of matter of claim 15 wherein said filler is alumina.

19. A method of preventing dental caries comprising impregnating a tooth with the interpolymer of claim 1.

20. A method of preventing dental caries comprising impregnating a tooth with the interpolymer of claim 1 and a polyalkylacrylate.

21. A method of preventing dental caries comprising depositing the composition of claim 1 on a tooth.

22. A method of preventing dental caries comprising use of a fixed or removable oral device fabricated by use of the interpolymer of claim 1.

* * * * *